United States Patent [19]
Bystedt et al.

[11] Patent Number: 5,595,132
[45] Date of Patent: Jan. 21, 1997

[54] SUPERSTRUCTURE FOR MULTIHULL VESSELS

[75] Inventors: Stig Bystedt, Uddevalla; Orvar Toreskog, Alingsås; Henrik Nordhammar, Göteborg, all of Sweden

[73] Assignee: Stena Rederi, AB, Göteborg, Sweden

[21] Appl. No.: 360,832

[22] Filed: May 30, 1995

[30] Foreign Application Priority Data

Jul. 9, 1992 [SE] Sweden .................................. 9202131

[51] Int. Cl.$^6$ ..................................................... B63B 1/00
[52] U.S. Cl. ............................................. 114/61; 114/65 R
[58] Field of Search .............................. 114/61, 264, 265, 114/65 R, 76, 78, 79 R, 85, 355, 356

[56] References Cited

U.S. PATENT DOCUMENTS

| | | | |
|---|---|---|---|
| 496,729 | 5/1893 | Fairchild | 114/264 |
| 522,348 | 7/1894 | Martini | 114/61 |
| 2,405,115 | 8/1946 | Creed | 114/61 |

OTHER PUBLICATIONS

Patent Abstracts of Japan, vol. 10, No. 62, M–460 (JP, A, 60–206797 Hitachi ZOSEN K.K., Oct. 18, 1985).

*Primary Examiner*—Edwin L. Swinehart
*Attorney, Agent, or Firm*—Keck, Mahin & Cate

[57] ABSTRACT

A catamaran vessel includes two hulls which are mutually connected by a cargo deck. A superstructure includes passenger spaces and is supported by a web structure which extends generally along each hull. Each longitudinal side wall of the superstructure is formed from a latticework beam whose plane is oriented generally vertically and whose longitudinal axis extends essentially horizontally. The latticework beams are fixedly connected to the wall structures. The floor and ceiling structures of the superstructure are connected to the latticework beams so as to greatly stiffen the superstructure and to render the beams highly resistant to bending forces. Consequently, the spaces defined between the longitudinal profiles of the beams and the struts are essentially free of deformation forces when the vessel is at sea. The spaces can be used essentially completely for windows, and the wall structures can be given a relatively low natural bending resistance.

5 Claims, 1 Drawing Sheet

U.S. Patent  Jan. 21, 1997  5,595,132
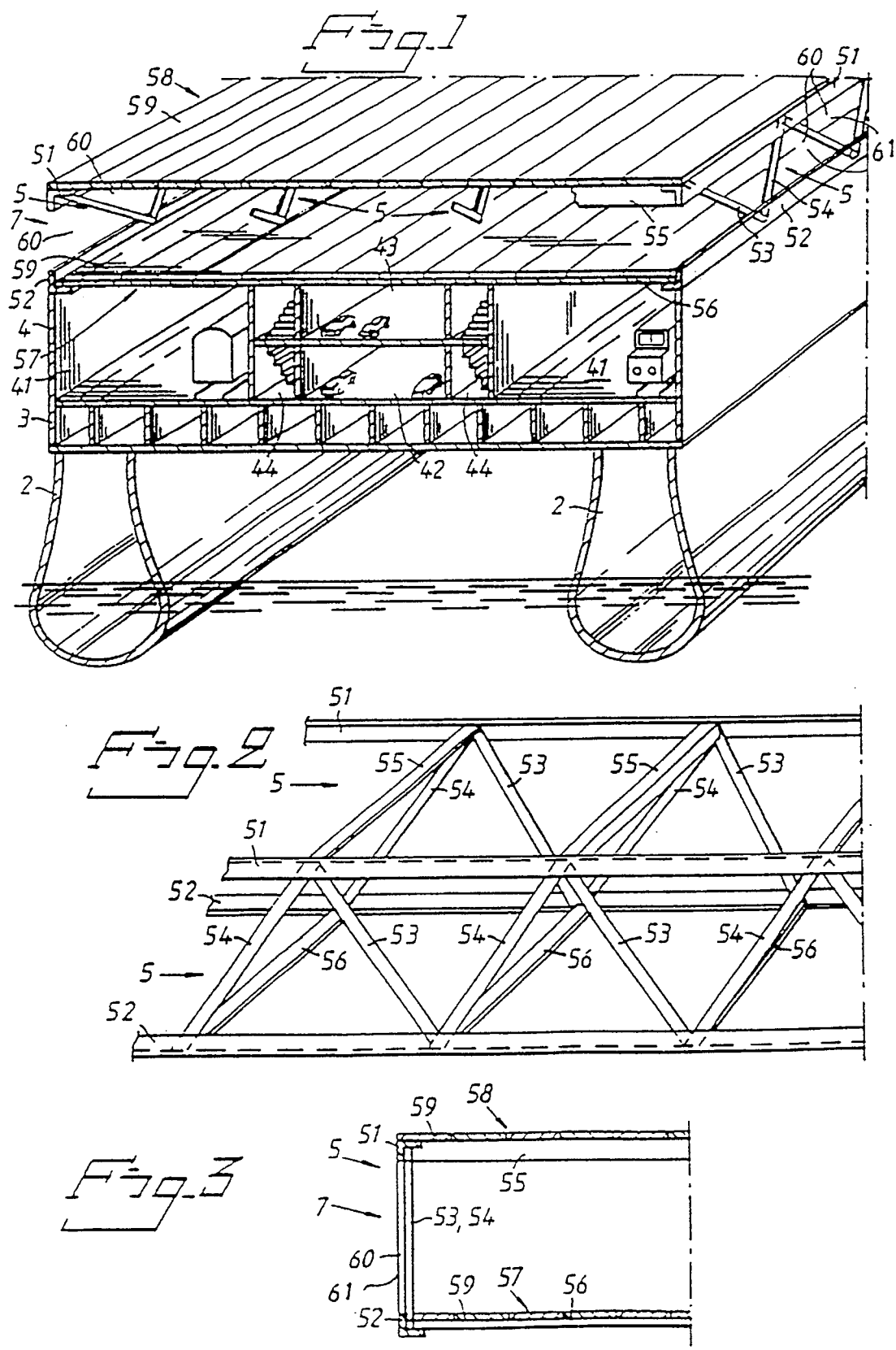

SUPERSTRUCTURE FOR MULTIHULL VESSELS

BACKGROUND OF THE INVENTION

1. Field of the Invention

The present invention relates to a multi-hull vessel of the catamaran type, which includes two or more hulls arranged in generally parallel and mutually spaced relationship and connected by means of one or more decks, and an overlying space in a superstructure which is supported by one or more wall structures extending from respective hulls.

2. Description of Related Art

High speed, seagoing multi-hull vessels are constructed of two or more slim mutually parallel hulls which are joined together by means of one or more decks, which often carry cargo, including motor vehicles. Built on top of the deck or decks is a superstructure for accommodating passengers. The superstructure is supported on one or more wall structures extending from respective hulls. In principle, the wall structures may consist of the sides of respective hulls or vertical extensions of said sides.

Large, high-speed catamarans may have a length of 100 meters, a hull height of about 12 meters, a width of 40 meters and propulsion machinery which will propel the vessel at a speed of 35 knots, for instance. The free space above the cargo deck may be 5 meters, for instance. It will be seen from these factors that when in motion, the vessel will be subjected to large bending and torsion stresses and also to large deformation forces, and that the aforesaid side walls are therefore conventional, simple metal plate walls which are extended the long sides of the superstructure, so as to form the stiffest possible side-beam structure together with respective hulls. Nevertheless, the stresses and deformation forces are still high in those regions which form the longside walls of the passenger space, which limits the possibility of providing window openings in these walls. In conventional seagoing vessels, it is necessary to round the window openings so as to reduce the risk of stress concentrations. In spite of this, however, the elastic deformation of these window openings still remains highly troublesome and places high demands on the elastic attachment of the window panes or window glass.

SUMMARY OF THE INVENTION

Accordingly, one object of the invention is to provide in multi-hull vessels of the aforesaid kind a superstructure construction which achieves a reduction in the deformation forces acting on the side walls of the passenger space, for instance, in operation, while providing the thus stiffened side-wall construction of the superstructure with larger free surfaces in which window glass, for instance, can be fitted. Alternatively, covering material can be fitted into the openings or on the frames.

This object is achieved with a vessel construction according to claim 1. Thus, in accordance with the invention, walls in the passenger space are constructed from shear-force absorbing latticework beams which extend in a generally vertical plane, said beams being firmly connected to those walls which support respective beams from the underlying hull. Each long side of the vessel will thus, in principle, include a rigid I-beam structure where, in the main, part of the roof structure of the superstructure and the uppermost part of the latticework beam and the lower part of the hull will form the flanges of the I-beam, and where the total wall structure, including the latticework beam, forms the web of the I-beam.

The longitudinal profiles of the latticework beams are conveniently connected to the roof or ceiling and the floor of the superstructure, wherein the floor may be constructed to enhance the bending resistance of the longitudinal profiles of the latticework frames.

The latticework frames may include straight zig-zag struts, all of which are inclined at an angle of, e.g., 60° to the longitudinal profiles of the latticework frames, wherein the free triangular surfaces of the frames can be filled essentially with window glass, so as to enable at least the major part of the side walls of the passenger space to consist of window glass.

Naturally, further latticework frames can be arranged within the passenger space, between its ceiling and floor, parallel with the latticework frames positioned along the sides, wherein the inner latticework frames may be mounted above the longitudinal and transverse bulkheads and stairwells which partition-off the underlying spaces both transversely and longitudinally.

In principle, the term shear-force absorbing latticework beams as used in the present context is meant to define two essentially parallel profiled elements which are mutually joined by struts that extend generally obliquely between the profiled elements and that are inclined in alternate directions. The struts may be straight, so as to form generally triangular openings in the beam. Alternatively, the struts may have the form of circles or ellipses which lie tangential to both the longitudinal profiles and to each other. The actual latticework frame itself imparts the desired shear-force stiffness to the superstructure walls, thereby enabling the walls to be covered with wall material without needing to take into account deformation forces or mechanical strength in regard of the actual vessel construction.

The invention and further developments thereof are set forth in the following claims.

BRIEF DESCRIPTION OF THE DRAWINGS

The invention will now be described in more detail with reference to exemplifying embodiments thereof and also with reference to the accompanying drawings, in which FIG. 1 is a schematic cross-section view of a catamaran constructed in accordance with the invention;

FIG. 2 is a sectional view of part of the catamaran superstructure supporting structure; and FIG. 3 is a cross-sectional view of an outer area of the catamaran superstructure.

DESCRIPTION OF THE PREFERRED EMBODIMENT

The vessel illustrated in FIG. 1 comprises two parallel hulls 2 which are mutually joined by a cargo deck 3. The wall structure 4 supports a superstructure 7 along the outer edge of each hull 2. The superstructure 7 includes passenger spaces, such as restaurants, cabins, etc.

The cargo deck 3 and the walls 4 define a cargo space, including space for motor vehicles. For instance, longitudinally extending bulkheads 44 may divide the cargo deck 3 transversely into sections, namely an outer, longitudinally extending section 41 for accommodating lorries, trucks, etc., wherein these spaces 41 may communicate with each other at one end of the vessel, for instance the forward end thereof. The central part of the cargo deck 3 may be divided by an intermediate floor structure into two stories 42, 43 for the accommodation of cars, etc. The bulkhead 44 may include an elevator (lift) and stairs for vertical communication.

The superstructure 7 is comprised of a plurality of flat latticework beams 5 whose longitudinal axes coincide essentially with the longitudinal axis of the vessel and the planes of which are vertical. In particular, a latticework beam 5 is provided along each long side of the superstructure 7. In the illustrated case, the superstructure includes four beams 5 which are spaced generally equidistant from one another, with the two central beams 5 each being located above an associated bulkhead 44.

Each latticework beam 5 includes two longitudinally extending profiled elements 51, 52 which are mutually joined by straight struts which extend in alternate directions. The beams 5 are mutually connected by transverse beams 55, 56 which are connected suitably to the point of intersection between the struts 53, 54 and the profile elements 51, 52.

Only very small changes will occur in the size and shape of the triangular free spaces 60 in the latticework beams 5 that form the longitudinal side of the superstructure 7, even when the vessel moves at high speed through a heavy sea. This enables the spaces 60 to be glazed essentially to their full extent, if so desired. Since the elements 51, 52 and the struts 53, 54 form only a very small part of the total surface area of the beams 5, the passenger space windows 61 may comprise a very large part of the walls of the superstructure 7.

Although not shown, the foreward and sternward wall of the superstructure 7 may be constructed in the same manner as the side walls, as can also the transverse walls which divide the superstructure 7 into several sections in the longitudinal direction of the vessel.

Naturally, not all of the free spaces 60 need be used as windows, and the architect is free to provide desired window sizes and shapes in a simple fashion and at low cost, within those limitations offered by the openings 60 of the latticework frames 5.

It will be seen from FIG. 3 that the floor 57 and ceiling 58 of the superstructure can be built from elongated, flat elements 59 which, in this case, must be dimensioned to withstand those stresses that are transmitted by the beam 5 to the floor 57 and the ceiling 58.

It will be understood that the invention is not restricted to the aforedescribed and illustrated embodiment and that modifications can be made within the scope of the inventive concept expressed in the following claims.

We claim:

1. A multi-hull catamaran comprising:
    at least two hulls which extend in a mutually parallel and horizontally spaced relationship,
    at least one deck joining said at least two hulls together,
    a superstructure, supported on said at least two hulls by at least one wall structure extending from said hulls and defining an overlying space, and
    latticework beams forming walls of the superstructure and having longitudinal profiles which extend horizontally and struts which extend between said profiles in alternating directions, said profiles and said struts lying in planes which are oriented generally vertically, the latticework beams being connected firmly to said at least one wall structure supporting the superstructure on the at least two hulls, free spaces defined by the longitudinal profiles and the struts in the latticework beams forming window openings for said overlying space.

2. A vessel according to claim 1, characterized in that said superstructure has a roof structure and a floor structure, the longitudinal profiles of the latticework beams are connected to the roof structure and the floor structure of the superstructure, and said floor structure and said roof structure contribute to an overall strength of the catamaran and strengthen a bending resistance of the longitudinal profiles of the latticework beams.

3. A vessel according to claim 1, and further comprising windows provided in the window openings formed by the free spaces.

4. A vessel according to claim 1, and further comprising material fitted in the free spaces defined in the latticework beams, said material being essentially free of appreciable deformation forces.

5. A vessel according to claim 1, characterized in that the beams take up shear forces.

* * * * *